(12) United States Patent
Doreswamy (10) Patent No.: US 10,327,628 B2
(45) Date of Patent: Jun. 25, 2019

(54) PEDIATRIC LARYNGOSCOPE, AND METHOD OF USE

(71) Applicant: Srinivasa Murthy Doreswamy, Mysuru (IN)

(72) Inventor: Srinivasa Murthy Doreswamy, Mysuru (IN)

(*) Notice: Subject to any disclaimer, the term of this patent is extended or adjusted under 35 U.S.C. 154(b) by 128 days.

(21) Appl. No.: 15/305,956

(22) PCT Filed: Apr. 22, 2015

(86) PCT No.: PCT/CA2015/000273
§ 371 (c)(1),
(2) Date: Oct. 21, 2016

(87) PCT Pub. No.: WO2015/161362
PCT Pub. Date: Oct. 29, 2015

(65) Prior Publication Data
US 2017/0042415 A1  Feb. 16, 2017

Related U.S. Application Data

(60) Provisional application No. 61/982,491, filed on Apr. 22, 2014.

(51) Int. Cl.
*A61B 1/267* (2006.01)
*A61B 1/00* (2006.01)
*A61B 1/07* (2006.01)
*A61B 1/06* (2006.01)
*A61B 1/04* (2006.01)

(52) U.S. Cl.
CPC .......... *A61B 1/267* (2013.01); *A61B 1/00124* (2013.01); *A61B 1/04* (2013.01); *A61B 1/0661* (2013.01); *A61B 1/0669* (2013.01); *A61B 1/0676* (2013.01); *A61B 1/07* (2013.01); *A61B 1/2673* (2013.01)

(58) Field of Classification Search
CPC .. A61B 1/04; A61B 1/06; A61B 1/267; A61B 1/2673
See application file for complete search history.

(56) References Cited

U.S. PATENT DOCUMENTS

| 4,425,909 A | | 1/1984 | Rieser et al. | |
|---|---|---|---|---|
| 4,799,485 A | * | 1/1989 | Furey | A61B 1/07 600/193 |
| 5,092,314 A | * | 3/1992 | Zeitels | A61B 1/267 600/194 |
| 5,363,840 A | * | 11/1994 | Silva | A61B 1/267 600/190 |
| 2006/0183978 A1 | * | 8/2006 | Howard | A61B 1/267 600/197 |

OTHER PUBLICATIONS

PCT—International Search Report. PCT/CA2015/000273, dated Jul. 22, 2015.
PCT—Written Opinion of the International Searching Authority. PCT/CA2015/000273, dated Jul. 22, 2015.

* cited by examiner

*Primary Examiner* — Zade Coley (57) ABSTRACT

A laryngoscope assembly having: a handle; an offset member having a first end coupled to said handle; and a blade coupled to a second of said offset member; and wherein said offset member is orthogonal to said handle and said blade, and disposes said blade away from said handle to increase visibility within a buccal cavity of a patient by placing said handle away from a line of sight of an operator when said blade is placed in said buccal cavity.

17 Claims, 11 Drawing Sheets

PEDIATRIC LARYNGOSCOPE, AND METHOD OF USE

FIELD OF THE INVENTION

The present invention relates to endotracheal intubation instruments, more particularly it relates to a laryngoscope.

DESCRIPTION OF THE RELATED ART

Laryngoscopes are well known in the art, and are used to visualize the larynx for proper diagnosis of laryngeal disorders, such as, vocal cord paralysis. They are also used to assist with the placement of a tube from a ventilator machine into a patient's trachea to aid with the oxygenation of the patient, a procedure commonly referred to as endotracheal intubation. Oftentimes, endotracheal intubation is performed pre-emptively to avoid serious emergencies in situations which may result in cessation of breathing unexpectedly, such as brain injury, brain infection, sepsis, serious multi-trauma, and metabolic derangement. In such emergency situations, the proper positioning of the laryngoscope and placement of the tube must be performed in a quick and safe manner.

Figure 1:
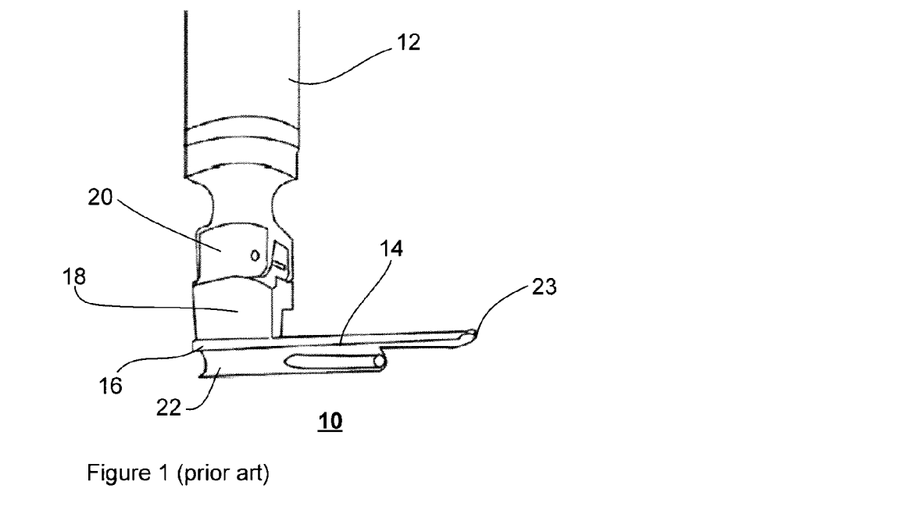
FIG. 1 shows a prior art laryngoscope.
Figure 2:
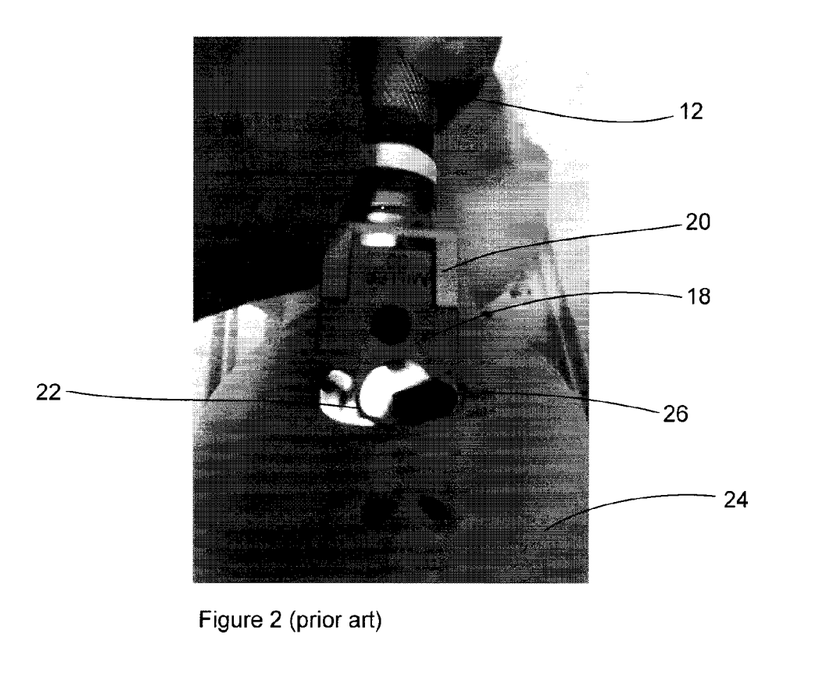
FIG. 2 shows the prior art laryngoscope of FIG. 1 in use.
Figure 3:
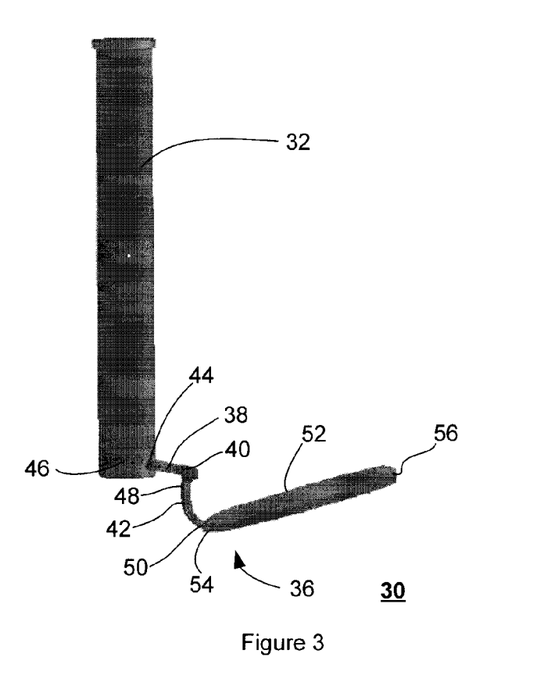
FIG. 3 shows a perspective view of a laryngoscope, in one exemplary embodiment.

Over the years, it has become common to intubate infants, especially neonates or premature newborns, and children in order to provide enhanced life support. While the market is awash with prior art pediatric laryngoscopes, these laryngoscopes are merely scaled-down versions of adult laryngoscopes, and are therefore not designed specifically for neonatal use. A typical prior art laryngoscope includes either a straight or curved blade which facilitates visualization of the patient's vocal cords which are used for locating the patient's larynx and subsequently the trachea. FIG. 1 shows one such prior art pediatric laryngoscope 10, in its normal operative downwardly directed position. Pediatric laryngoscope 10 includes a handle 12 extending upward and a curved tubular blade 14, which are disengagably connectable with one another. At its proximal end 16, the relatively large blade 14 is provided with blade mount 18 with a hinge which permits blade 14 to be releasably secured to the handle 14 via hinge lock 20 disposed at one end of the handle 14. Blade 14 is relatively thick and includes a curved longitudinal or lateral web 22 extending from the blade mount 18 for suppressing a patient's tongue, such that a distal end 23 of blade 14 exposes the larynx. While these attributes and features are useful or essential in adult laryngoscopes, these features may be non-essential or ill-suited for pediatric applications. For example, in an adult laryngoscope, bulky hinge lock 20 is designed to have a locking system that remains stable with the weight of adult head and counter weight applied by the operator. Since adults and older children have sufficiently large mouths and the bulky nature of the hinge lock 20 of an adult laryngoscope is not a great issue. However, when used with pediatric patients 24, such as neonates, particularly preterm newborns, with relatively small mouths, then the blade mount 18 and bulky hinge lock 20 occupy a substantial portion of mouth 26, as can be seen in FIG. 2.

It is evident that when used on a pediatric patient 24, blade mount 18 and bulky hinge lock 20 appear directly in the line of sight of the operator, and therefore substantially obstructs the view of the larynx. Also, while the lateral web 22 of blade 14 is useful for suppressing an adult patient's tongue to prevent the tongue from encroaching into the line of sight, in a premature newborn with a relatively small mouth, the lateral web 22 with its relatively large footprint further contributes to a decrease in the area of vision. Additionally, the overall structure of the blade 14 often results in the requirement of intensive pressure to move the anatomical structures to expose the larynx. In exerting the required pressure, the operator is sometimes forced to pry against the patient's upper teeth, thereby increasing the possibility of damage to the teeth, gums, lips, and jaw, which is undesirable, especially in pediatric patients 24. Generally, use of the prior art laryngoscope requires extensive training, for example, proper positioning of the blade 14 requires a series of manoeuvres of the operator's shoulder, which may place the operator in awkward, and non-ergonomic positions, and may be tiresome in certain challenging emergency cases.

It is an object of the present invention to mitigate or obviate at least one of the above-mentioned disadvantages.

SUMMARY OF THE INVENTION

In one of its aspects, there is provided a laryngoscope assembly having:
a handle;
an offset member having a first end coupled to said handle; and
a blade coupled to a second end of said offset member; and
wherein said offset member is orthogonal to said handle and said blade, and disposes said blade away from said handle to increase visibility within a buccal cavity of a patient by placing said handle away from a line of sight of an operator when blade is placed in the buccal cavity.

In another of its aspects, there is provided a laryngoscope assembly having:
a handle;
an offset member having one end coupled to said handle; and
a blade coupled to another end of said offset member.

In another of its aspects, there is provided a laryngoscope blade assembly having:
a blade mount removably attached to a handle;
an offset member extending from said blade mount;
a blade comprising an intra-oral portion and an extra-oral blade portion;
and
wherein blade mount comprises a first longitudinal axis, offset member comprises a second longitudinal axis, said extra-oral blade portion comprises a third longitudinal axis, and said intra-oral blade portion comprises a fourth longitudinal axis, such that said second longitudinal axis of said offset member is orthogonal to said first longitudinal axis of said blade mount and said third longitudinal axis of said extra-oral blade portion, and said fourth longitudinal axis of said intra-oral blade portion is orthogonal to said third longitudinal axis of said extra-oral blade portion.

In another of its aspects, there is provided a method of performing laryngoscopy comprising the steps of:
providing a laryngoscope having a handle, an offset member and a blade;
said offset member having a proximal end coupled to said handle via blade mount and a proximal end coupled to a blade, said blade comprising a curved extra-oral blade portion and an intra-oral blade portion; wherein blade mount comprises a first longitudinal axis, said offset member comprises a second longitudinal axis, said extra-oral blade portion comprises a third longitudinal axis, and said intra-oral blade portion comprises a fourth longitudinal axis, such that said second longitudinal axis of offset member is orthogonal to said first longitudinal axis of said blade mount and third longitudinal axis of said extra-oral blade portion, and said fourth longitudinal axis of said intra-oral blade portion is orthogonal to said third longitudinal axis of said extra-oral blade portion;

holding said handle in one hand and inserting said intra-oral blade portion into an open buccal cavity of a patient in a supine position, with said curved extra-oral blade portion over a lip of said patient;

positioning said intra-oral blade portion for laryngeal exposure; and whereby said offset member disposes said blade away from said blade mount to increase visibility within said buccal cavity by placing said handle away from a line of sight when said blade is placed in the buccal cavity to provide a substantially unobstructed view within said buccal cavity for said laryngeal exposure.

Advantageously, the laryngoscope optimizes laryngeal exposure, and therefore facilitates endotracheal intubation, especially in a neonate, and substantially diminishes the likelihood of trauma to the surrounding oral structures during intubation, thereby enhancing safety. In addition, the laryngoscope is intuitive and therefore can be used easily without additional training.

BRIEF DESCRIPTION OF THE DRAWINGS

Several exemplary embodiments of the present invention will now be described, by way of example only, with reference to the appended drawings in which.

DETAILED DESCRIPTION OF EXEMPLARY EMBODIMENTS

The detailed description of exemplary embodiments of the invention herein makes reference to the accompanying block diagrams and schematic diagrams, which show the exemplary embodiment by way of illustration and its best mode. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented.

Moreover, it should be appreciated that the particular implementations shown and described herein are illustrative of the invention and its best mode and are not intended to otherwise limit the scope of the present invention in any way. Indeed, for the sake of brevity, certain sub-components of the individual operating components and other functional aspects of the systems may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

Figure 4:
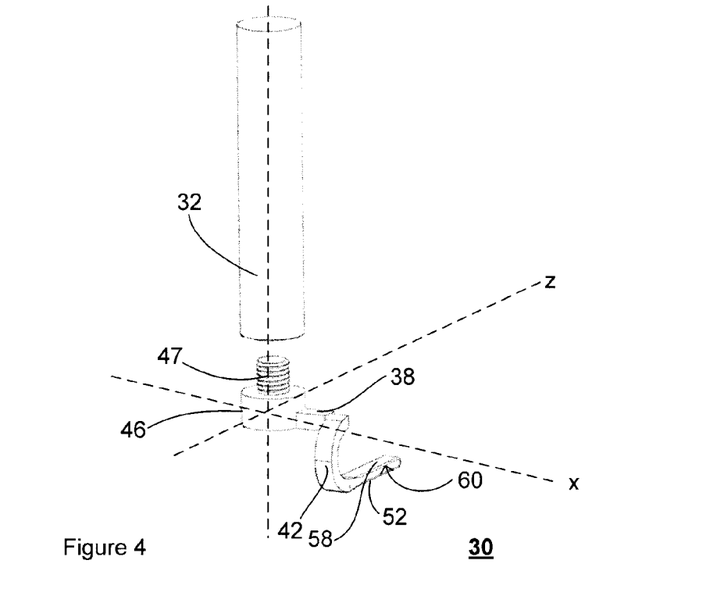
FIG. 4 shows an exploded view of the laryngoscope.
Figure 5A:
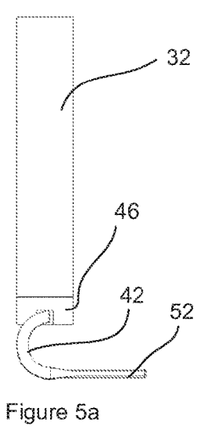
FIG. 5a shows a side view of the laryngoscope.
Figure 5B:
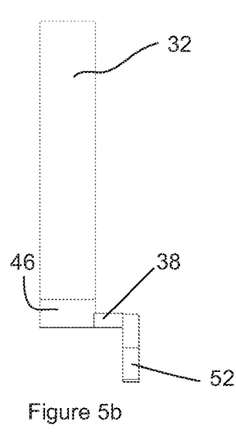
FIG. 5b shows a back view of the laryngoscope.
Figure 5C:
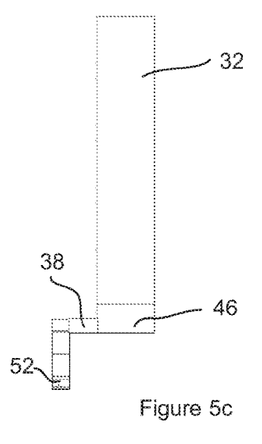
FIG. 5c shows a front view of the laryngoscope.
Figures 5D, 5E, 5F:
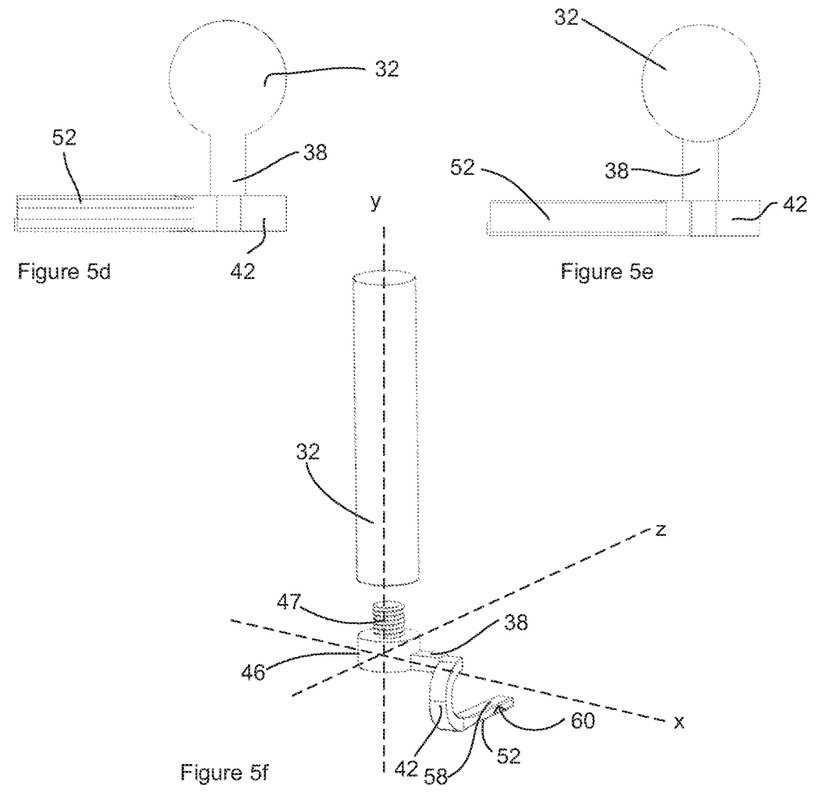
FIG. 5d shows a top view of the laryngoscope.
FIG. 5e shows a bottom view of the laryngoscope.
FIG. 5f shows a perspective view of the laryngoscope.
Figure 6:
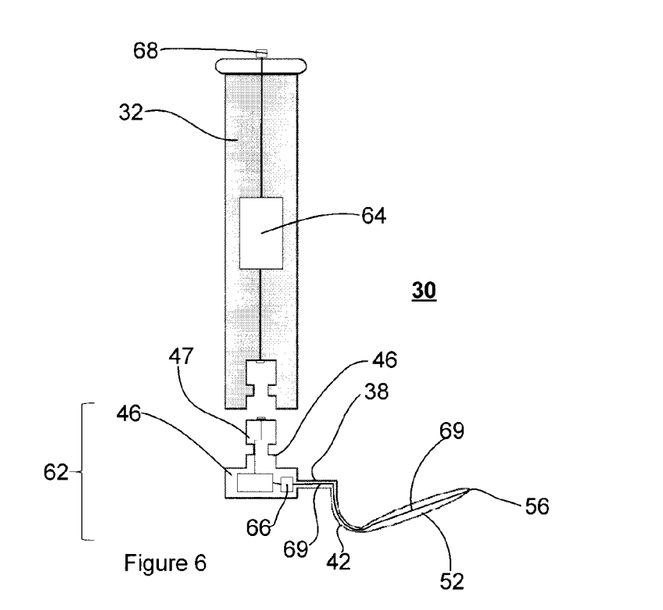
FIG. 6 shows a schematic diagram of the laryngoscope.

Looking at FIGS. 3, 4 and 5a to 5f, there is shown a laryngoscope assembly, generally designated by the numeral 30, in one exemplary embodiment. Laryngoscope assembly 30 may be used in pediatric patients, and comprises a handle 32 having a longitudinal axis A, and an interchangeable laryngoscope blade 36 attached thereto via an offset member 38. Accordingly, one end 40 of the offset member 38 includes an extra-oral blade portion 42, and other end 44 includes a blade mount 46 removably attached to handle 32 via a fastening mechanism 47, such as threaded engagement (as shown in FIG. 4), or coaxial engagements, tab and slot engagement (as shown in FIG. 6) or friction fit. The extra-oral blade portion 42 has a proximal portion 48 joined to end 40 of the offset member 38, and a distal portion 50. The extra-oral blade portion 42 is curved between proximal portion 48 and distal portion 50, and has a predetermined radius of curvature which defines an angle that conforms to the oral anatomy of the patient, as will be described later. Unitarily extending from distal portion 50 of arcuate extra-oral blade portion 42 is intra-oral blade portion 52 having a longitudinal body with a proximal end 54 and a distal tip 56, and laterally straight therebetween. Alternatively, intra-oral blade portion 52 is curved between the longitudinal edges thereof.

Preferably offset member 38 includes a relatively small cross-sectional area and a minimal footprint to increase visibility of the interior of a buccal cavity of the patient. Offset member 38 includes a rectangular cross-section in a plane orthogonal to handle 32 along the entire length of offset member 38. Alternatively, offset member 38 includes a cylindrical cross-section.

The intra-oral blade portion 52 comprises an elongate body that is generally flat with an upper surface 58 and an opposite lower surface 60. The offset member 38, extra-oral blade portion 42 and intra-oral blade portion 52 may be integrally formed. Accordingly, a unitary component formed of these elements 38, 42, and 52 results in fewer crevices that may trap contaminants, and therefore facilitates cleaning and sterilization.

Housed within the mount 46 is an illumination system 62 which provides light within the buccal cavity when intra-oral portion 52 is placed therein. Illumination system 62 is electrically coupled to a power source 64 for energizing light source 66 and activated by switch 68, as shown in FIG. 6. Preferably, power source 64 is included with handle 32, and may include one or batteries (not shown) and associated power circuitry (not shown). Light source 66 may be an LED, and may include a light guide 69 to irradiate a portion of blade 36, such as the intra-oral portion 52, or irradiate a region adjacent to distal tip 56 of the intra-oral portion 52. Accordingly, a suitable bore to receive the light guide 69 may be formed within offset member 38, extra-oral blade portion 42 and intra-oral blade portion 52. Alternatively, light source 66 may be disposed adjacent to distal tip 56.

Figure 7:
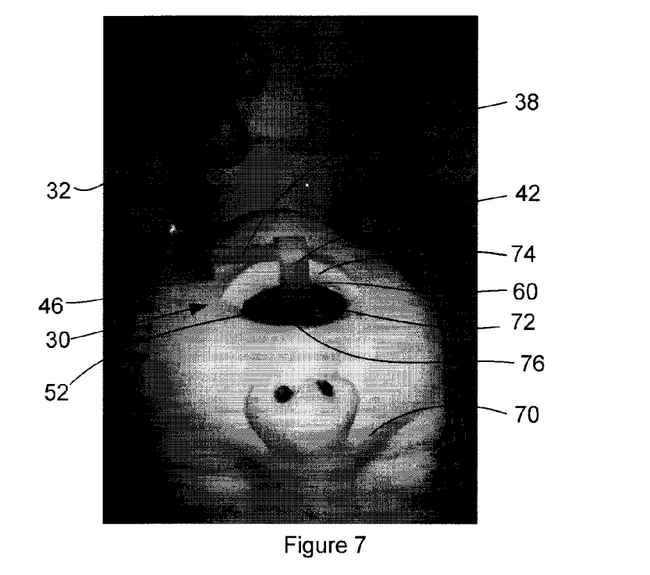
FIG. 7 shows the laryngoscope in use.
Figure 8A:
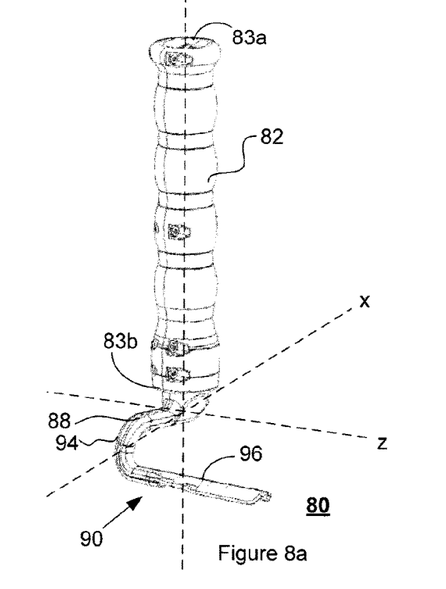
FIG. 8a shows a perspective view of a laryngoscope, in another exemplary embodiment.
Figure 8B:
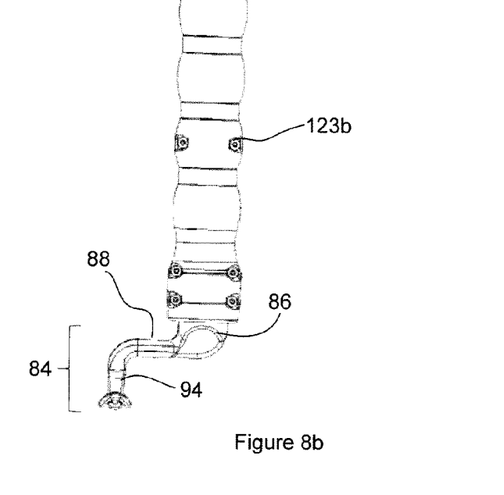
FIG. 8b shows a front view of the laryngoscope.
Figure 8C:
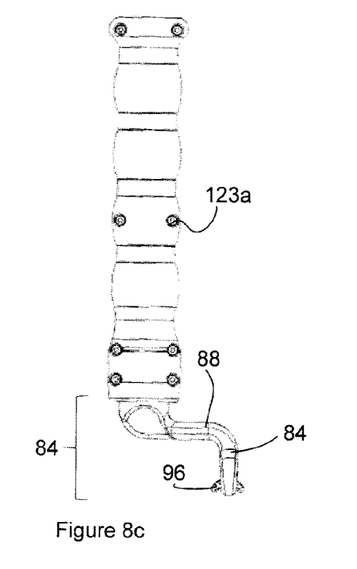
FIG. 8c shows a back view of the laryngoscope.
Figure 8D:
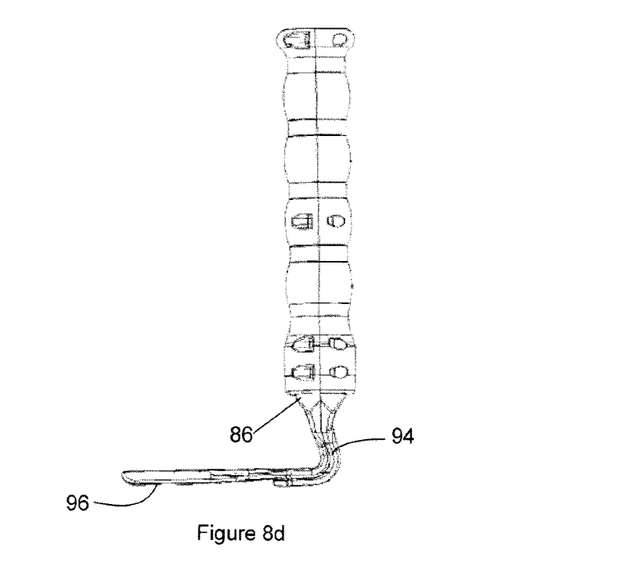
FIG. 8d shows a side view of the laryngoscope.
Figure 8E:
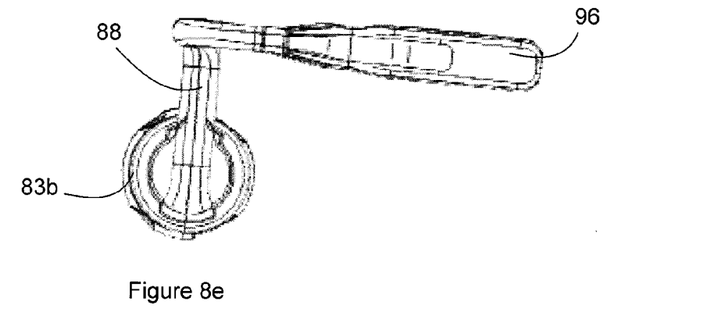
FIG. 8e shows a bottom view of the laryngoscope.
Figure 8F:
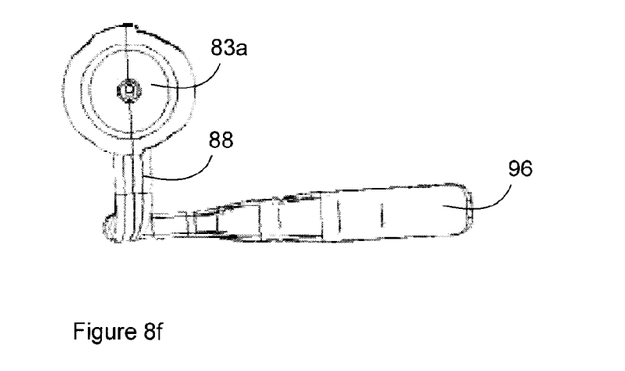
FIG. 8f shows a top view of the laryngoscope.

In operation, as shown in FIG. 7, pediatric patient 70 lies supine on an operating table and the operator is positioned adjacent to the head of pediatric patient 70 for an overhead view. After proper positioning of the patient 70, the patient's buccal cavity 72 is opened, in neonates 70 this action may be accomplished by a scissor technique involving the operator's thumb and middle finger of one hand. With the other hand, the operator holds the laryngoscope 30 by handle 32 and positions intra-oral blade portion 52 inside the patient's buccal cavity 72. Offset member 38 places handle 32 at a sufficient distance away from blade 36 such that handle 32 does not obstruct the line of sight of the operator when blade 36 is inserted in the buccal cavity 72.

With the intra-oral blade portion 52 in the operating position, a light switch 68 is operated to energize light source 66 and the light emitted by the light source 66 is directed to a light guide 69 which transmits the light to the distal tip 56 of the intra-oral blade portion 52 to focus the light for optimal laryngeal exposure. Alternatively, intra-oral blade portion 52 may be formed of a translucent material such that light is also emitted along the length of the light guide 69.

A portion of the offset member 38 adjacent end 40 is caused to rest substantially below bottom lip 74 of the patient 70, while the arcuate extra-oral blade portion 42 abuts an upper surface of bottom lip 74. Using a wrist motion, the operator causes the upper surface 58 of the intra-oral blade portion 52, to push on the tongue, to place the tongue out of the line of sight. Since the arcuate extra-oral blade portion 42 curves around the bottom lip 74 and bottom teeth, extensive force is not required to use the laryngoscope 30, and therefore excessive force is not exerted on the bottom lip 74 and bottom teeth, which would otherwise cause trauma thereto. Meanwhile, the distal tip 56 of the intra-oral blade portion 52 pushes on the base of the epiglottis to move the epiglottis out of the line of sight and to thereby expose the larynx.

As can be seen in FIG. 7, the blade 36 is disposed away from upper lip 76 and upper teeth of the patient 70, thereby substantially minimizing or eliminating any possible trauma thereto, common with prior art pediatric laryngoscopes. Therefore, visibility within the buccal cavity 72 of a neonate patient 70 is greatly improved by providing a blade 36 having a minimal footprint and by the positioning of the handle 32 and blade mount 46 away from the blade 36 via offset member 38.

Advantageously, laryngoscopy procedures in which laryngoscope 30 is used are substantially faster and easier to perform than procedures employing prior art pediatric laryngoscopes, and require no extra training or retraining. Consequently, higher laryngoscopy success rates are achievable, especially in emergency situations, which translates to increased operator satisfaction, and minimal discomfort for the neonate patients 70.

FIGS. 8a to 8e show various views of laryngoscope 80, in another exemplary embodiment. Laryngoscope 80 may be used in pediatric patients, and includes handle 82 with top end 83a and bottom end 83b attached to a head sub-assembly 84 comprising blade mount 86, offset member 88 and laryngoscope blade 90. Blade mount 86 is removably attached to handle 82 via a fastening mechanism 92 (not shown), and laryngoscope blade 90 is attached thereto via offset member 88, such that head sub-assembly 84 may be interchangeable to allow a variety of blades 90 of different dimensions to be used. Laryngoscope blade 90 is formed of an extra-oral blade portion 94, and intra-oral blade portion 96. Generally, handle 82, as well as blade mount 86, includes a longitudinal axis A along a y-axis, offset member 88 includes a longitudinal axis B along an x-axis, extra-oral blade portion 94 includes a longitudinal axis C parallel to the y-axis, and intra-oral blade portion 96 includes a longitudinal axis D parallel to a z-axis.

Figure 9A:
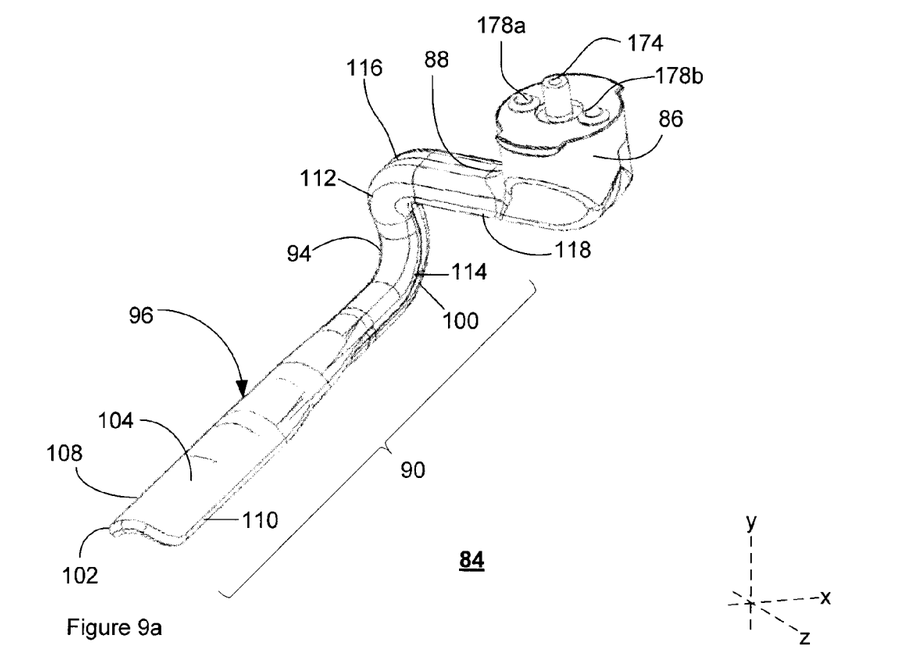
FIGS. 9a to 9b show various views of a head-sub assembly of the laryngoscope.
Figure 9B:
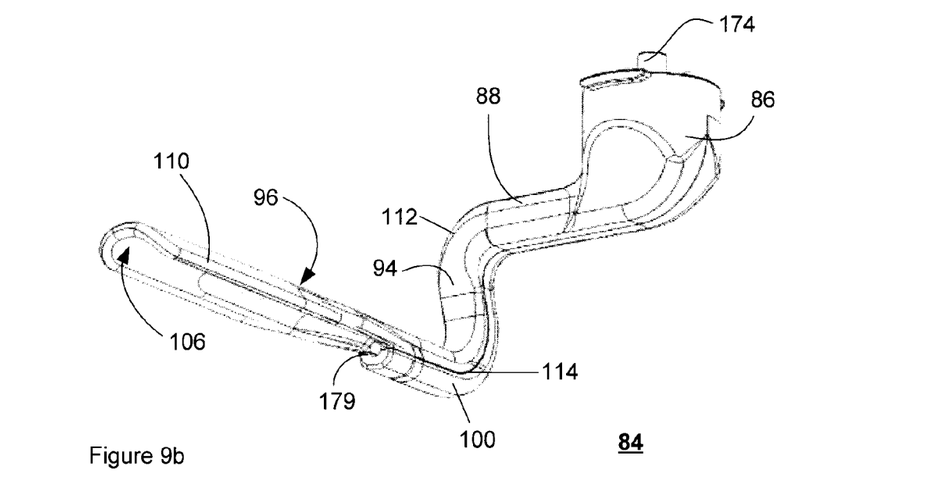

FIGS. 9a to 9b show various views of the head sub-assembly 84 of laryngoscope 80. Laryngoscope blade 90 comprises longitudinally extending intra-oral blade portion 96 with has proximal end 100, distal end 102, a palatal (or upper) surface 104, lingual (or lower) surface 106, and a pair of opposed longitudinal edges 108 and 110. Palatal surface 104 and lingual surface 106 are non-planar, such that the longitudinal body of intra-oral blade portion 96 is curved between longitudinal edges 108 and 110, or substantially concave. The curvature of the intra-oral blade body portion 96 and "spooned tip" of distal end 102 generally fits the contour of the oropharynx of a patient, in operation.

Extra-oral blade portion 94 includes a longitudinally extending body with first end 112 and second end 114. As can be best illustrated in FIG. 9b, second end 114 is integrally formed with proximal end 100 of intra-oral portion 96, such that the longitudinal axis C of extra-oral blade portion 94 forms an angle of approximately 90 degrees with the longitudinal axis D of intra-oral portion 96. Accordingly, handle 82 and extra-oral portion 94 are generally parallel to one another.

Offset member 88 includes a longitudinally extending body with blade end 116 and mount end 118. Blade end 116 is integrally formed with first end 112 of extra-oral portion 94, such that the longitudinal axis B of offset member 88 forms an angle of approximately 90 degrees with the longitudinal axis C of extra-oral portion 94. Mount end 118 of offset member 88 is integrally formed with blade mount 86, and longitudinal axis B of offset member 88 forms an forms an angle of approximately 90 degrees with the longitudinal axis A of blade mount 86. Blade mount 86 is removably attached to bottom end 83b of the handle 82 via fastening mechanism, and locked thereto while in operation, as will be described later.

Figure 10:
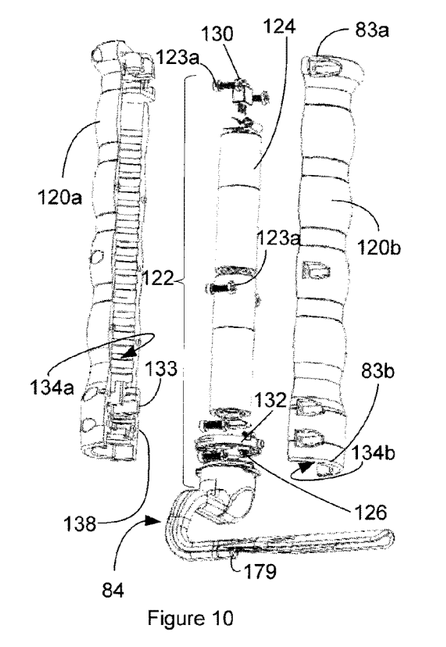
FIG. 10 shows an exploded view of the laryngoscope.
Figure 11:
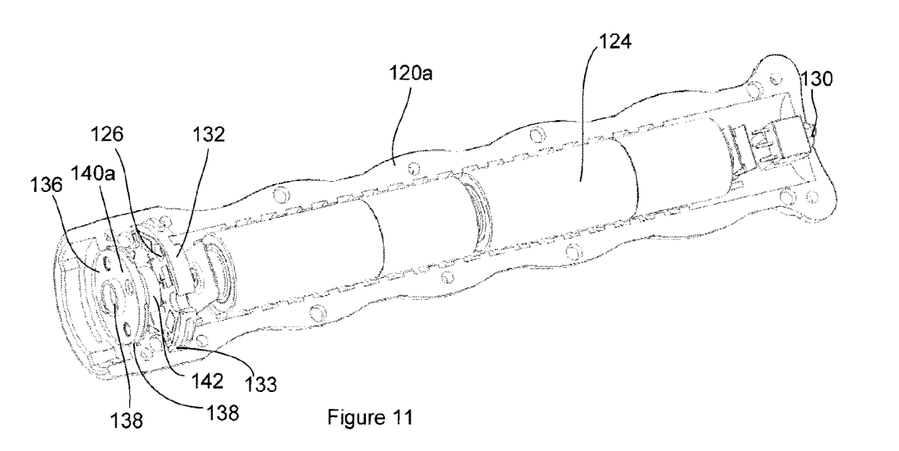
FIG. 11 shows a cut-away view of a handle of the laryngoscope.

FIG. 10 shows an exploded view of a laryngoscope 80. Handle 82 is composed of two complementary shells 120a, 120b which form a cavity for housing an illumination system 122 for providing light to the buccal cavity of a patient. As can be seen in greater detail in FIG. 11, the illumination system 122 comprises a power supply, such as batteries 124, a printed circuit board (PCB) 126 having power circuitry electrically coupled to a light source, such as an LED 128, via a switch 130, and a light guide 131. PCB 126 is secured to PCB holder 132 which is received in a circumferential channel 133 within an interior wall 134a, 134b (not shown) of shells 120a, 120b, respectively. Detent plate 136 is received in a circumferential channel 138 within interior walls 134a and 134b adjacent to bottom end 83b. Detent plate 136 includes an aperture 139 extending between two opposed surfaces 140a, 140b, thereof. Gasket light block 142 having a channel 144 (not shown) abuts surface 140b of detent plate 136 and PCB 126 such that LED 128 is received within channel 144, or LED 128 is positioned adjacent to channel 144 such that light from LED 128 is received and guided by channel 144.

Figure 12A:
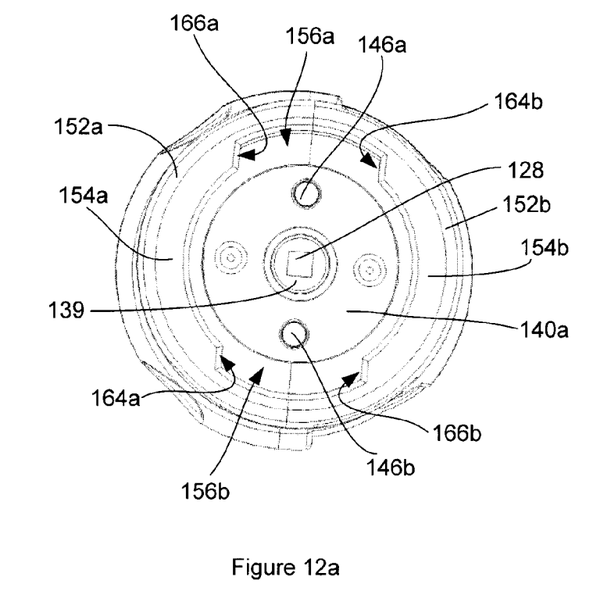
FIG. 12a shows a front view of an opening of a handle of the laryngoscope.
Figure 12B:
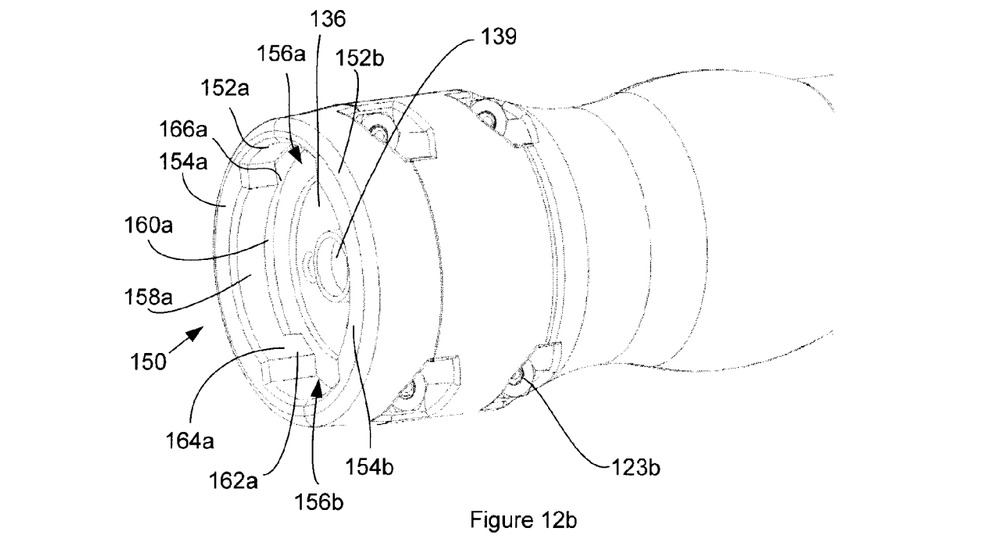
FIG. 12b shows a perspective view of the opening of the handle.

As can be seen in FIGS. 12a and 12b, detent plate 136 also includes apertures 146a, 146b facing opening 150 adjacent to bottom end 83b of handle 82. Walls 152a, 152b extending from about circumferential channel 138 include opposed flanges 154a, 154b with gaps 156a, 156b therebetween. Below each of the flanges 154a, 154b, is a shoulder 158a, 158b (not shown) which defines a passageway 160a, 160b, between shoulders 158a, 158b and detent plate 136. Each of the shoulders 158a, 158b include an arm 162a, 162b at one end 164a, 164b formed therewith and extending to abut detent plate 136, such that the passageways 160a, 160b may only be accessed via open end 166a, 166b of passageways 160a, 160b, respectively.

Figure 13:
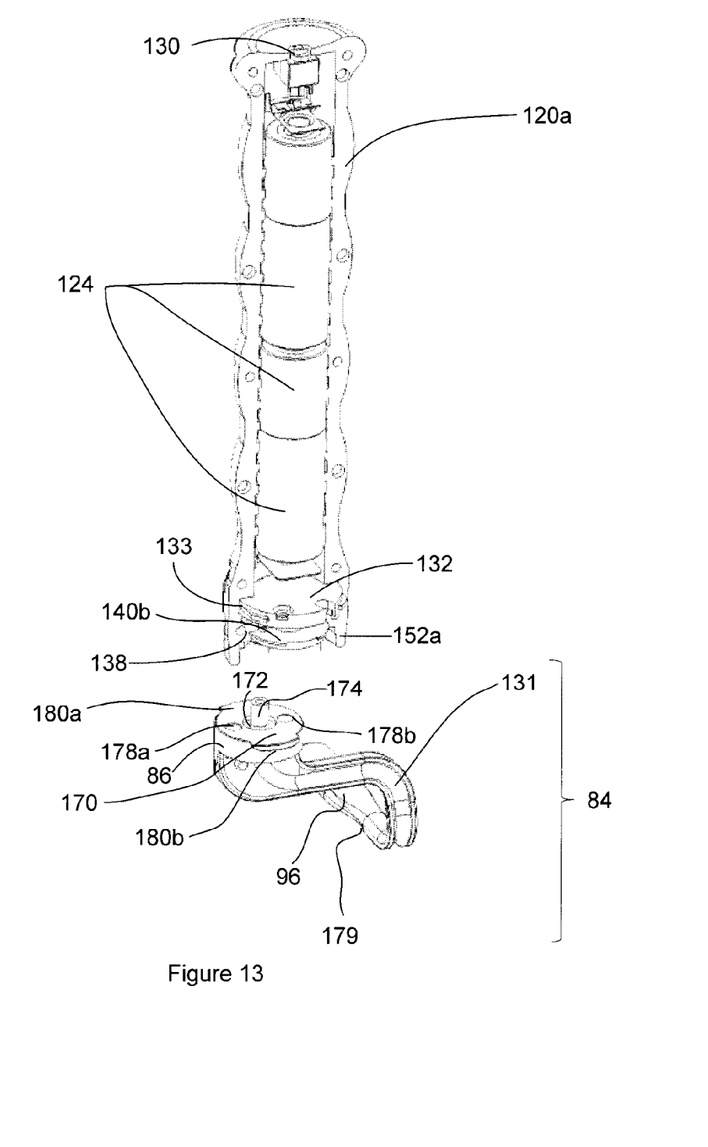
FIG. 13 shows a cut-away view of the handle and the head-sub assembly.

As can be seen in FIG. 13, blade mount 86 includes a mounting plate 170 with an orifice 172 having one end 174 of a light guide 131 extending therethrough, and detents 178a, 178b. Light guide 131 is formed within blade mount 86, offset member 88, extra-oral portion 94, and intra-oral portion 96. Other end 179 is located on lingual (or lower) surface 106, adjacent to proximal end 100 of intra-oral portion 96. Mounting plate 170 is dimensioned to fit into opening 150, and includes opposed tabs 180a, 180b. In order to secure blade assembly 90 to the handle 82, opposed tabs 180a, 180b are introduced into gaps 156a, 156b, and end 174 of light guide 131 engages circumferential channel 138 in detent plate 136. Blade assembly 90 is advanced towards detent plate 136 such that mounting plate 170 is in close proximity with detent plate 136, and detents 178a, 178b abut detent plate 136. A force is applied to head sub-assembly 84 to cause rotation thereof in one direction, such that opposed tabs 180a, 180b enter passageways 160a, 160b via open ends 166a, 166b and are caused to travel along passageways 160a, 160b. The force is applied until opposed tabs 180a, 180b abut arms 162a, 162b, and detents 178a, 178b are received by apertures 146a, 146b, thereby locking the head sub-assembly 84 to the handle 82. In order to remove the blade assembly 90 from the handle 82, a force in the opposite direction is applied, and detents 178a, 178b escape apertures 146a, 146b, and the opposed tabs 180a, 180b are caused to travel along passageways 160a, 160b towards open ends 166a, 166b, and opposed tabs 180a, 180b are extricated from opening 150 via gaps 156a, 156b, while end 174 of light guide 131 exits circumferential channel 139 in detent plate 136. As such, fastening mechanism 92 comprises features of detent plate 136, opening 150 and mounting plate 170 and allows the head sub-assembly 84 to be removably coupled to the handle 82.

Accordingly, when illumination system 122 is enabled via switch 130, light from LED 128 is guided via channel 144 of gasket light block 142 to end 174 of light guide 131 within circumferential channel 139 of detent plate 136, and via the length of light guide 131 to exit at end 179 on lingual (or lower) surface 106, and further guided towards distal end 102 of the blade 90, and into the buccal cavity.

In another embodiment, intra-oral blade portion 52, or 96 comprises a "C" cross-sectional shape. It should be understood other blade geometries may be used with embodiments of the laryngoscope 30, or 80.

In another embodiment, laryngoscope blade 36, or 90 is unitary with the handle 32, or 82, or may be attached to the handle 32, or 82 via suitable engagements between these components as would be recognized by one of ordinary skill in the art, such as ultrasonic welding, among others.

Figure 14A:
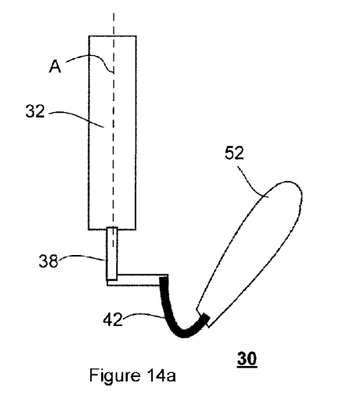
FIGS. 14a to 14d show views of a laryngoscope, in another exemplary embodiments.

In yet another embodiment, offset member 38, or 88 is L-shaped, with one portion extending from one end of handle 32, or 82 along the longitudinal axis A of handle 32, or 82, and an orthogonal portion coupled to the extra-oral blade portion 42, or 94 at one end, as shown FIG. 14a.

Figure 14B:
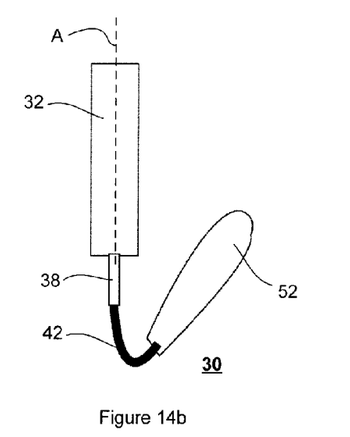

In yet another embodiment, offset member 38, or 88 extends from one end of handle 32, or 82 along the longitudinal axis A of handle 32, or 82, as shown in FIG. 14b.

Figure 14C:
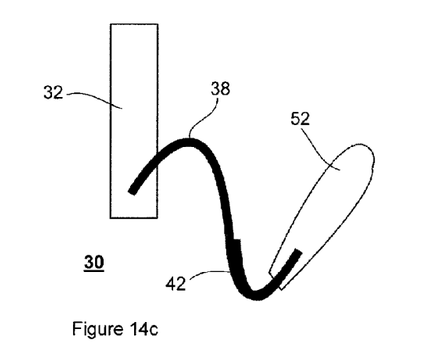

In yet another embodiment, offset member 38, or 88 is curved, and extends from a wall of handle 32, or 82, as shown in FIG. 14c.

In yet another embodiment, offset member 38, or 88 is hingedly connected to handle 32, or 82 which facilitates pivotal movement of offset member 38, or 88 with respect to handle 32 or 82.

Figure 14D:
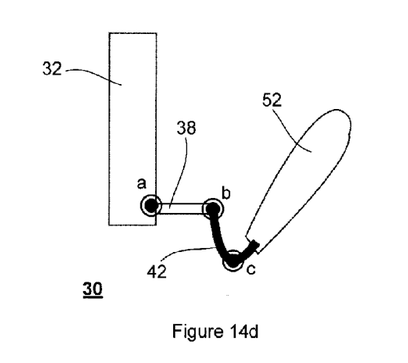

In yet another embodiment, handle 32, or 82, offset member 38, or 88, extra-oral blade portion 42 or 94, and intra-oral blade portion 52, or 96 are hingedly connected to each other at points a, b, c, for placing and locking the laryngoscope blade 36, or 90 in a plurality of positions to suit the operator and the patient, as shown in FIG. 14d.

In yet another embodiment, offset member 38, or 88 is extensible.

In yet another embodiment, laryngoscope 30 or 80 further includes a blade sheath, which may be disposable, or reusable and autoclavable. Similarly, handle 32, or 82 may also include a disposable, or a reusable and autoclavable handle sheath.

In yet another embodiment, laryngoscope 30 or 80 includes a viewing member cooperating with illumination system 62, or 122 to provide for remote viewing at distal tip 56, or 102 using a suitable eyepiece.

In yet another embodiment, laryngoscope 30 or 80 includes a camera mounted adjacent to distal tip 56, or 102 of intra-oral blade portion 52 or 96 for capturing images within the buccal cavity 72. The captured data may be transmitted via a wired connection or wirelessly for storage on a computer-readable medium and/or for viewing via a suitable display.

In yet another embodiment, laryngoscope 30, or 80 includes an illumination system 62, or 122 incorporated within handle 32 or 82, and may include additional light guides 69, 131 associated therewith.

Laryngoscope 30 or 80 may be produced from a variety of materials, for example, such as stainless steel or suitable plastics which may provide for disposability or a degree of flexibility in blade 36 or 90.

In yet another embodiment, laryngoscope 30 or 80 is integrally formed, such that handle 32, offset member 38, extra-oral blade portion 42, and intra-oral blade portion 52, are formed as a unitary piece. Similarly, in yet another embodiment, laryngoscope 80 is integrally formed, such that handle 82, blade mount 86, offset member 88, extra-oral blade portion 94, and intra-oral blade portion 96, are formed as a unitary piece.

It is also anticipated herein that blades incorporating the features of the claimed invention may be provided which are adaptable for use with various prior art laryngoscope handles, which are currently in use, to provide the advantages herein disclosed.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims. As used herein, the terms "comprises," "comprising," or any other variations thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical."

The preceding detailed description of exemplary embodiments of the invention makes reference to the accompanying drawings, which show the exemplary embodiment by way of illustration. While these exemplary embodiments are described in sufficient detail to enable those skilled in the art to practice the invention, it should be understood that other embodiments may be realized and that logical and mechanical changes may be made without departing from the spirit and scope of the invention. For example, the steps recited in any of the method or process claims may be executed in any order and are not limited to the order presented. Further, the present invention may be practiced using one or more servers, as necessary. Thus, the preceding detailed description is presented for purposes of illustration only and not of limitation, and the scope of the invention is defined by the preceding description, and with respect to the attached claims.

The invention claimed is:

1. A laryngoscope assembly having:
   a handle;
   an offset member having a first end coupled to said handle; and
   a blade coupled to a second end of said offset member; and
   wherein said offset member is orthogonal to said handle and said blade, and disposes said blade away from said handle to increase visibility within a buccal cavity of a patient by placing said handle away from a line of sight of an operator when said blade is placed in said buccal cavity;
   wherein said first end comprises a mount couplable to said handle via at least one of a threaded engagement, a fastening mechanism, a friction fitting, a tab and slot arrangement, a coaxial engagement; and
   wherein said blade comprises a curved extra-oral blade portion and an intra-oral blade portion comprising an elongate and flat body.

2. The laryngoscope assembly of claim 1, wherein said extra-oral blade portion comprises a proximal portion joined to said second end of said offset member, and a distal portion.

3. The laryngoscope assembly of claim 2, wherein said intra-oral blade portion comprises a proximal end unitarily extending from said distal portion of said curved extra-oral blade portion and terminating at a distal tip, such that said extra-oral blade portion and said intra-oral blade portion are integrally formed.

4. The laryngoscope assembly of claim 3, wherein said extra-oral blade portion is curved between said proximal portion and said distal portion to form an arcuate portion.

5. The laryngoscope assembly of claim 4, wherein said intra-oral blade portion comprises an elongate body that is flat with an upper surface and an opposite lower surface.

6. The laryngoscope assembly of claim 5, wherein said offset member comprises a relatively small cross-sectional area and a minimal footprint within an interior of said buccal cavity to increase visibility of said interior of the buccal cavity.

7. The laryngoscope assembly of claim 6, wherein said offset member comprises at least one of a rectangular cross-section and a cylindrical cross-section in a plane orthogonal to said handle along an entire length of said offset member.

8. The laryngoscope assembly of claim 7, wherein said offset member is L-shaped, with one portion extending from one end of said handle along a longitudinal axis of said handle, and an orthogonal portion coupled to said extra-oral blade portion.

9. The laryngoscope assembly of claim 7, wherein said offset member is curved, with one portion extending from a wall of said handle and a curved portion coupled to said extra-oral blade portion.

10. The laryngoscope assembly of claim 7, wherein said offset member is hingedly connected to said handle at one end to facilitate pivotal movement of said offset member with respect to said handle, wherein said blade is placed in at least of one of a plurality of positions to suit an operator and said patient, and secured in at least one of said plurality of positions.

11. The laryngoscope assembly of claim 7, wherein at least one of said handle, said offset member, said extra-oral blade portion and said intra-oral blade portion are hingedly connected to each other.

12. The laryngoscope assembly of claim 1, wherein said mount is removably attached to said handle.

13. The laryngoscope assembly of claim 12, further comprising an illumination system to provide light within said buccal cavity when said intra-oral blade portion is placed therein.

14. A laryngoscope assembly having:
   a handle;
   an offset member having one end coupled to said handle;
   a blade coupled to another end of said offset member; and
   wherein said one end is coupled to said handle via a blade mount, and said blade comprises an intra-oral blade portion and an extra-oral blade portion; and wherein said blade mount comprises a first longitudinal axis, said offset member comprises a second longitudinal axis, said extra-oral blade portion comprises a third longitudinal axis, and said intra-oral blade portion comprises a fourth longitudinal axis, such that said second longitudinal axis of offset member is orthogonal to said first longitudinal axis of said handle and third longitudinal axis of said extra-oral blade portion, and said fourth longitudinal axis of said intra-oral blade portion is orthogonal to said and third longitudinal axis of said extra-oral blade portion.

15. The laryngoscope assembly of claim 14, wherein said extra-oral blade portion comprises a curved body, and said intra-oral blade portion comprises a longitudinal planar body.

16. The laryngoscope assembly of claim 14, wherein said extra-oral blade portion comprises a curved body, and said intra-oral blade portion comprises a longitudinal body having opposed longitudinal edges such that said longitudinal body is curved between said opposed longitudinal edges.

17. A method of performing laryngoscopy comprising the steps of:
   providing a laryngoscope having a handle, an offset member and a blade; said offset member having a proximal end coupled to said handle via a blade mount and a proximal end coupled to said blade, said blade comprising a curved extra-oral blade portion and an intra-oral blade portion; wherein said blade mount comprises a first longitudinal axis, said offset member comprises a second longitudinal axis, said extra-oral blade portion comprises a third longitudinal axis, and said intra-oral blade portion comprises a fourth longitudinal axis, such that said second longitudinal axis of said offset member is orthogonal to said first longitudinal axis of said blade mount and said third longitudinal axis of said extra-oral blade portion, and said fourth longitudinal axis of said intra-oral blade portion is orthogonal to said third longitudinal axis of said extra-oral blade portion; wherein said extra-oral blade portion comprises a curved body, and said intra-oral blade portion comprises a longitudinal body having opposed longitudinal edges such that said longitudinal body is curved between said opposed longitudinal edges;

holding said handle in one hand and inserting said intra-oral blade portion into an open buccal cavity of a patient in a supine position, with said curved extra-oral blade portion over a lip of said patient;

positioning said intra-oral blade portion for laryngeal exposure; and whereby said offset member disposes said blade away from said blade mount to increase visibility within said buccal cavity by placing said handle away from a line of sight when said blade is placed in the buccal cavity to provide a substantially unobstructed view within said buccal cavity for said laryngeal exposure.

\* \* \* \* \*